United States Patent
Ou et al.

(10) Patent No.: US 8,269,963 B2
(45) Date of Patent: Sep. 18, 2012

(54) TUNABLE APPARATUS FOR PERFORMING SERS

(75) Inventors: Fung Suong Ou, Palo Alto, CA (US); Min Hu, Sunnyvale, CA (US); Wei Wu, Palo Alto, CA (US); Zhiyong Li, Redwood City, CA (US); R Stanley Williams, Portola Valley, CA (US)

(73) Assignee: Hewlett-Packard Development Company, L.P., Houston, TX (US)

(*) Notice: Subject to any disclaimer, the term of this patent is extended or adjusted under 35 U.S.C. 154(b) by 153 days.

(21) Appl. No.: 12/771,779

(22) Filed: Apr. 30, 2010

(65) Prior Publication Data

US 2011/0267608 A1    Nov. 3, 2011

(51) Int. Cl.
*G01J 3/44* (2006.01)
(52) U.S. Cl. ........................................ 356/301
(58) Field of Classification Search .............. 356/72–73, 356/301
See application file for complete search history.

(56) References Cited

U.S. PATENT DOCUMENTS

| 2007/0015288 A1 | 1/2007 | Hulteen et al. |
| 2007/0086001 A1* | 4/2007 | Islam et al. .................. 356/301 |
| 2010/0062226 A1 | 3/2010 | Hulteen et al. |

FOREIGN PATENT DOCUMENTS

WO    WO 2006/138442 A2    12/2006

* cited by examiner

*Primary Examiner* — Tarifur Chowdhury
*Assistant Examiner* — Abdullahi Nur

(57) ABSTRACT

A tunable apparatus for performing Surface Enhanced Raman Spectroscopy (SERS) includes a deformable layer and a plurality of SERS-active nanoparticles disposed at one or more locations on the deformable layer, wherein the one or more locations are configured to be illuminated with light of a pump wavelength to cause Raman excitation light to interact with the nanoparticles and produce enhanced Raman scattered light from molecules located in close proximity to the nanoparticles. In addition, a morphology of the deformable layer is configured to be controllably varied to modify an intensity of the Raman scattered light produced from the molecules.

20 Claims, 11 Drawing Sheets

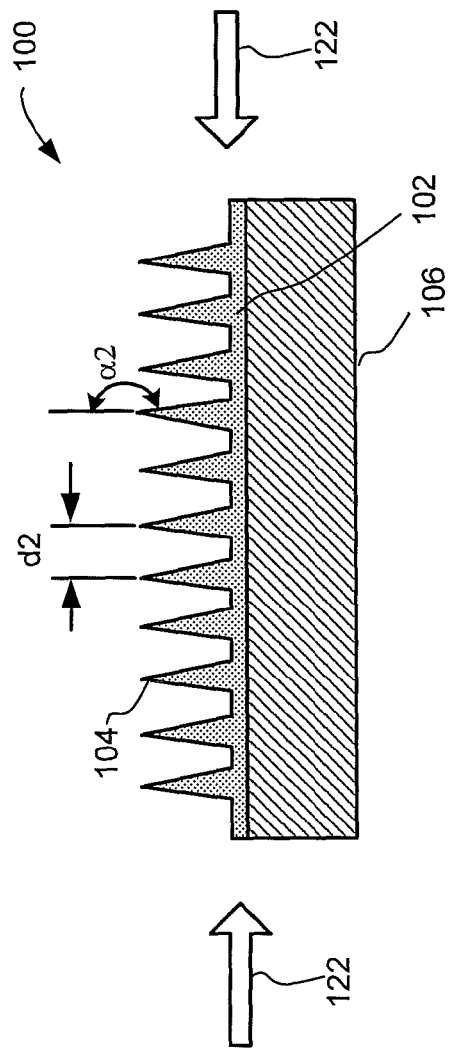
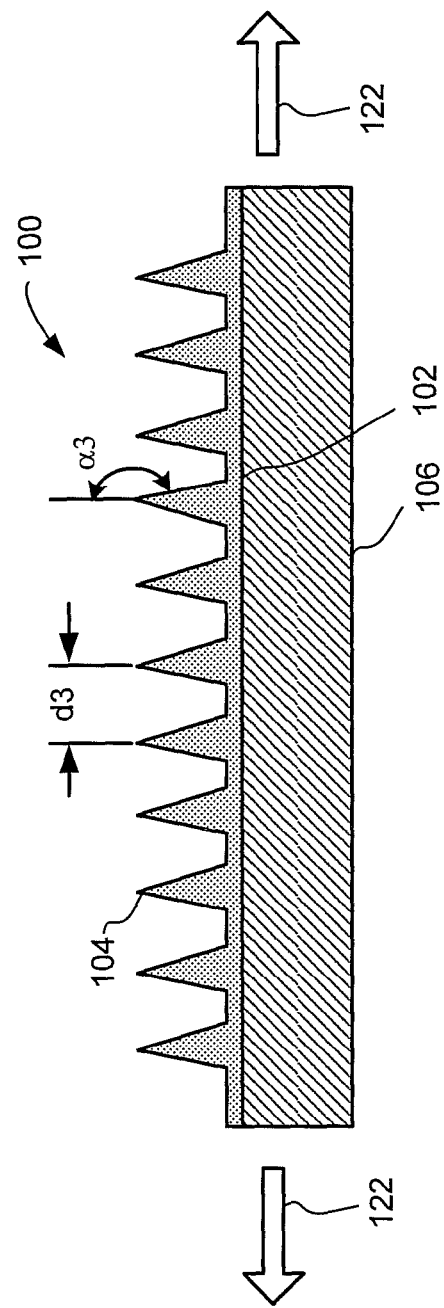

TUNABLE APPARATUS FOR PERFORMING SERS

GOVERNMENT LICENSE RIGHTS

This invention was made in the course of research partially supported by grants from the U.S. Government, under contract number HR0011-09-3-0002. The U.S. Government has certain rights in the invention.

CROSS-REFERENCE TO RELATED APPLICATIONS

The present application is related to commonly assigned and copending PCT patent application PCT/US2008/083827, filed on Nov. 17, 2008; PCT patent application PCT/US2009/1052308, filed on Jul. 30, 2009; U.S. patent application Ser. No. 12/771,440, filed on Apr. 30, 2010; U.S. patent application Ser. No. 12/771,753, filed on Apr. 30, 2010; and U.S. patent application Ser. No. 12/771,824, filed on Apr. 30, 2010, the disclosures of which are hereby incorporated by reference in their entireties.

BACKGROUND

Raman spectroscopy is a spectroscopic technique used in condensed matter physics and chemistry to study vibrational, rotational, and other low-frequency modes in molecular systems. In a Raman spectroscopic experiment, a monochromatic beam of light of a particular wavelength range passes through a sample of molecules and a spectrum of scattered light is emitted. The term "light" is not limited to electromagnetic radiation with wavelengths that lie in the visible portion of the electromagnetic spectrum but also includes electromagnetic radiation with wavelengths outside the visible portion, such as the infrared and ultraviolet portions of the electromagnetic spectrum, and can be used to refer to both classical and quantum electromagnetic radiation. The spectrum of wavelengths emitted from the molecule is called a "Raman spectrum" and the emitted light is called "Raman scattered light." A Raman spectrum can reveal electronic, vibrational, and rotational energies levels of a molecule. Different molecules produce different Raman spectrums that can be used like a fingerprint to identify molecules and even determine the structure of molecules.

The Raman scattered light generated by a compound (or ion) adsorbed on or within a few nanometers of a structured metal surface can be $10^3$-$10^{12}$ times greater than the Raman scattered light generated by the same compound in solution or in the gas phase. This process of analyzing a compound is called surface-enhanced Raman spectroscopy ("SERS"). In recent years, SERS has emerged as a routine and powerful tool for investigating molecular structures and characterizing interfacial and thin-film systems, and even enables single-molecule detection. Engineers, physicists, and chemists continue to seek improvements in systems and methods for performing SERS.

BRIEF DESCRIPTION OF THE DRAWINGS

Embodiments are illustrated by way of example and not limited in the following figure(s), in which like numerals indicate like elements, in which:

FIGS. 1B-1D, respectively, show cross-sectional views along a line A-A, shown in FIG. 1A of the SERS-active apparatus under varying morphology changes, according to embodiments of the invention;

DETAILED DESCRIPTION

For simplicity and illustrative purposes, the principles of the embodiments are described by referring mainly to examples thereof. In the following description, numerous specific details are set forth in order to provide a thorough understanding of the embodiments. It will be apparent however, to one of ordinary skill in the art, that the embodiments may be practiced without limitation to these specific details. In other instances, well known methods and structures are not described in detail so as not to unnecessarily obscure the description of the embodiments.

Embodiments of the present invention are directed to tunable apparatuses for performing surface-enhanced Raman spectroscopy. The apparatuses include a deformable layer having an array of nano-scale protrusions whose morphologies are tunable to vary performance of enhanced Raman spectroscopy by the apparatuses. In addition, SERS-active nanoparticles are disposed on the outer surface of the nano-scale protrusions and, in certain embodiments, near the ends, or tips, of the nano-scale protrusions. With optical pumping, the nano-scale protrusions emit Raman excitation light, which may be varied through modification of morphologies of the nano-scale protrusions. In this regard, the Raman excitation light emitted at different morphologies of the nano-scale protrusions may be detected and the morphology that results in the emission of the highest Raman excitation light may be identified.

I. Optically Operated SERS-active Systems

Figure 1A:
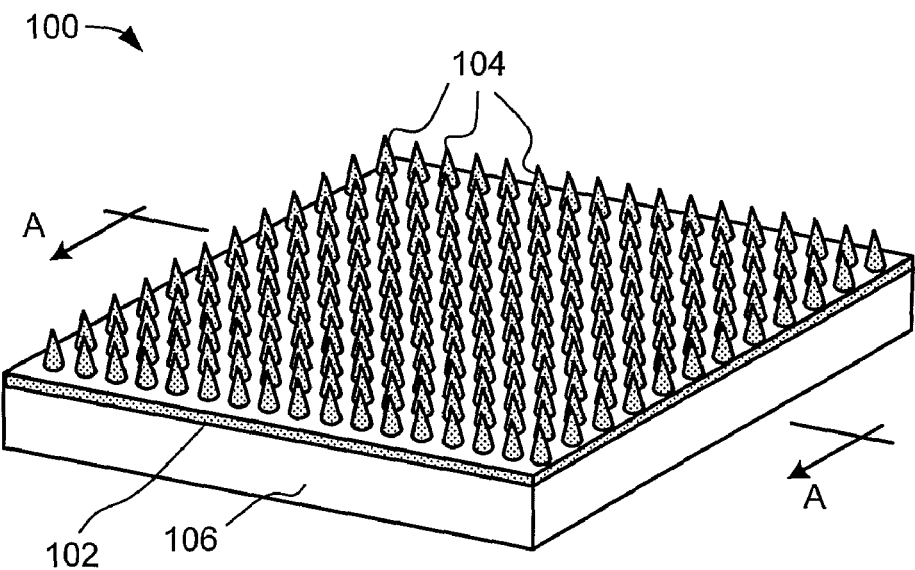
FIG. 1A shows an isometric view of a tunable SERS-active apparatus, according to an embodiment of the invention.

FIG. 1A shows an isometric view of a tunable SERS-active apparatus 100 configured in accordance with embodiments of the present invention. It should be understood that the apparatus 100 depicted in FIG. 1 may include additional components and that some of the components described herein may be removed and/or modified without departing from a scope of the apparatus 100. It should also be understood that the components depicted in FIG. 1 are not drawn to scale and thus, the components may have different relative sizes with respect to each other than as shown therein.

The apparatus 100 includes a deformable layer 102 that includes a plurality of nano-scale protrusions 104 extending above the deformable layer 102. The nano-scale protrusions 104 may be integrally formed with the deformable layer 102 or may be separately formed from the deformable layer 102. As shown in the example of FIG. 1A, the nano-scale protrusions 104 are configured to taper away from a top surface of the deformable layer 102, and have an initial radius of curvature of about between 10 to 1000 nm. In addition, the nano-scale protrusions 104 are depicted as being randomly distributed, but may also be arranged in a predetermined configuration to therefore distribute the nano-scale protrusions 104 in a substantially uniform density. Furthermore, although the nano-scale protrusions 104 have been depicted as being cone-shaped, the nano-scale protrusions 104 may be shaped as pillars, pyramids, hemispheres, etc., or have amorphous shapes, without departing from a scope of the apparatus 100. According to a particular example, the heights of the nano-scale protrusions 104 are about 1 micron and the distances between the tips of the nano-scale protrusions 104 are initially between about 100 nm to 500 nm. In another example, the distances between the tips of the nano-scale protrusions 104 are sub-wavelength. In another example, the distances are in a range of wavelength to sub-wavelength.

The deformable layer 102 is also depicted as being disposed on a substrate 106, which may provide structural support to the deformable layer 102. In one example, the deformable layer 102 is attached to the substrate 106 and thus, the substrate 106 is also formed of any of the deformable materials discussed below with respect to the deformable layer 102. In this example, the deformable layer 102 and the substrate 106 may be operated to have the same or similar rate of deformation. In another example, the deformable layer 102 is separately movable from the substrate 106 and thus may have a different rate of deformation than the substrate 106. In this example, the substrate 106 may be composed of a dielectric material, including glass, $SiO_2$, $Al_2O_3$, or any other suitable material, such as a metal or semiconductor. In addition, or alternatively, the deformably layer 102 may also include a dielectric material similar to the substrate 106. In other examples, the substrate 106 may be omitted from the apparatus 100.

Figure 1B:
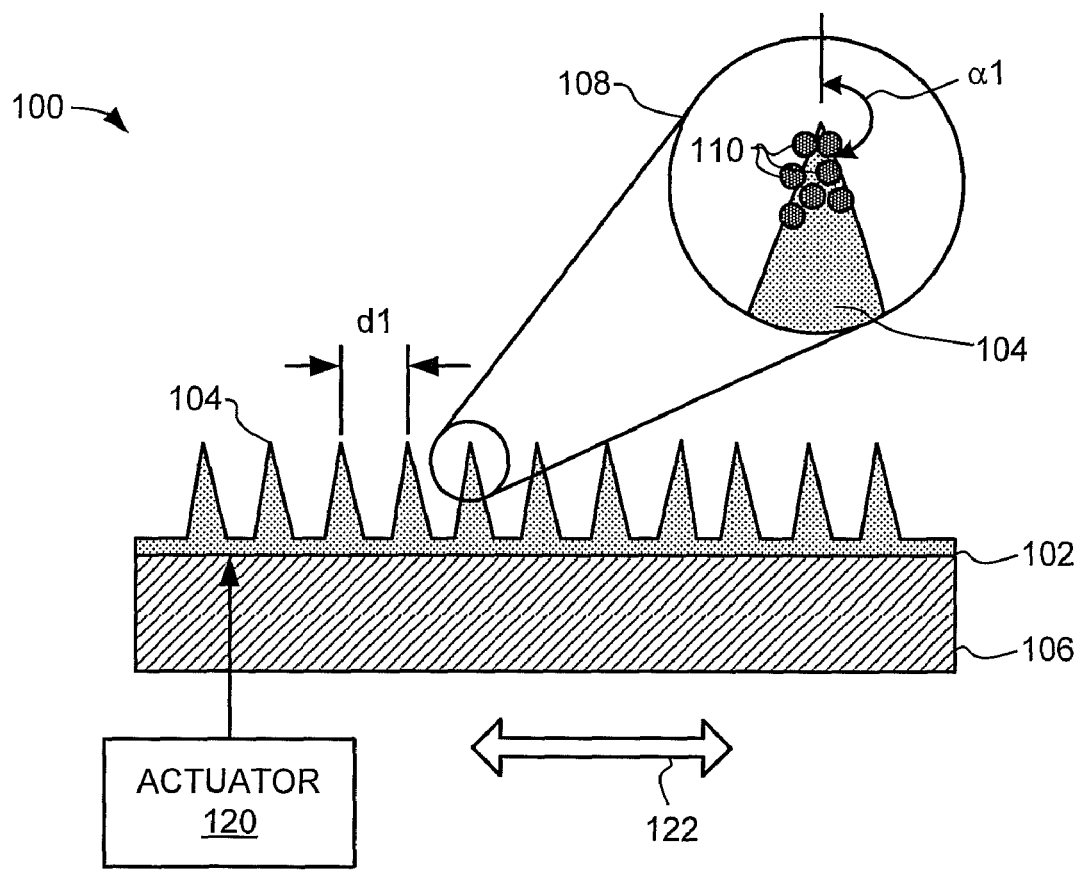

Turning now to FIG. 1B, there is shown a cross-sectional view along a line A-A, shown in FIG. 1A, of the apparatus 100, in accordance with an embodiment of the present invention. In the example of FIG. 1B, the nano-scale protrusions 104 may have a symmetric or an asymmetric, inverted-cone shape. In addition, the end of a nano-scale protrusion 104 is magnified in the enlargement 108, which reveals that the nano-scale protrusion 104 includes a plurality of SERS-active nanoparticles 110 disposed on the outer surface, near the tip, of the nano-scale protrusion 104. Note that embodiments of the present invention are not limited to nanoparticles 110 disposed over just the tips of the nano-scale protrusions 104. In other embodiments, the nanoparticles 110 may be disposed over nearly the entire surface of the nano-scale protrusions 104. In any regard, the SERs-active nanoparticles 110 may deposited onto the deformable layer 102 through, for instance, PVD, CVD, sputtering, etc., of metallic material, or self-assembly of pre-synthesized nanoparticles.

The deformable layer 102 and the nano-scale protrusions 104 may be composed of materials enabling the nano-scale protrusions 104 to be operated as gain media when the SERS-active apparatus 100 is optically pumped. For example, the deformable layer 102 and the nano-scale protrusions 104 may be composed of a direct or an indirect semiconductor material. Direct semiconductors are characterized by the valence band maximum and the conduction band minimum occurring at approximately the same wavenumber. As a result, an electron in the conduction band recombines with an unoccupied electronic state in the valence band giving off the energy difference as a photon of light. In contrast, indirect semiconductors are characterized by the valence band maximum and the conduction band minimum occurring at different wavenumbers. An electron in the conduction band minimum recombines with an unoccupied electronic state in the valence band maximum by first undergoing a momentum change followed by a change in electronic energy.

Indirect and direct semiconductors may be elemental and compound semiconductors. Indirect elemental semiconductors include silicon (Si) and germanium (Ge), and compound semiconductors include III-V materials, where Roman numerals III and V represent elements in the IIIa and Va columns of the Periodic Table of the Elements. Compound semiconductors can be composed of column IIIa elements, such as aluminum (Al), gallium (Ga), and indium (In), in combination with column Va elements, such as nitrogen (N), phosphorus (P), arsenic (As), and antimony (Sb). Compound semiconductors may also be further classified according to the relative quantities of III and V elements. For example, binary semiconductor compounds include GaAs, InP, InAs, and GaP; ternary compound semiconductors include GaAsyP1-y, where y ranges from greater than 0 to less than 1; and quaternary compound semiconductors include InxGa1-xAsyP1-y, where both x and y independently range from greater than 0 to less than 1. Other types of suitable compound semiconductors include II-VI materials, where II and VI represent elements in the IIb and VIa columns of the periodic table. For example, CdSe, ZnSe, ZnS, and ZnO are examples of binary II-VI compound semiconductors.

In addition or alternatively to the materials listed above, the deformable layer 102 and the nano-scale protrusions 104 are formed of a material that is configured to be deformable through application or interaction with an external force and/or element. By way of example, the deformable layer 102, the nano-scale protrusions 104, and the substrate 106, are formed of a flexible material, such as, polydimethylsiloxane (PDMS) elastomer, polyimide, polyethylene, polypropelene, etc., configured to be deformed through application of a mechanical force, such as, for instance, by a mechanical stage with micrometer resolution. In another example, the deformable layer 102, the nano-scale protrusions 104, and the substrate 106 are formed of one or more piezoelectric materials configured to be deformed through application of an electrical force. In a further example, the deformable layer 102, the nano-scale protrusions 104, and the substrate 106, are formed of a sheet of material configured to be deformed through application of an electrostatic force. In a yet further example, the deformable layer 102, the nano-scale protrusions 104, and the substrate 106 are formed of a material configured to be deformed through receipt of thermal energy, one or more chemicals, water, etc. By way of particular example, deformation of the deformable layer 102 and the nano-scale protrusions 104 may be driven by the deformation of the substrate 106.

Also shown in FIG. 1B is an actuator 120 configured to interact with either or both the deformable layer 102 and the substrate 106 to controllably vary the morphology of the deformable layer 102. In one example, the actuator 120 is configured to interact with the deformable layer 102 and/or the substrate 106 to cause the deformable layer 102 and/or the substrate 106 to contract and/or expand as denoted by the arrow 122. Examples of the expansion and contraction of the deformable layer 102 and the substrate 106 are shown in FIGS. 1C and 1D. The actuator 120 may interact with the deformable layer 102 and/or the substrate 106 through one or more of mechanical, electrical, thermal, and/or chemical, interactions as discussed above. The actuator 120 may thus be selected to interact appropriately with the material forming the deformable layer 102.

As depicted in FIGS. 1B-1D, as the deformable layer 102 is expanded or contracted, the morphologies of the nano-scale protrusions 104, such as, the spacings between the nano-scale protrusions 104, the angles of the nano-scale protrusions 104, the heights of the nano-scale protrusions 104 become varied. This change in the morphologies of the nano-scale protrusions 104 is depicted in FIGS. 1B-1D. More particularly, the angles at the tips of nano-scale protrusions 104 are depicted as changing from a1 to a2 and a3 and the distances between the nano-scale protrusions 104 are depicted as changing from d1 to d2 and d3 in FIGS. 1B-1D, respectively. Although not explicitly depicted, the heights of the nano-scale protrusions 104 also vary among FIGS. 1B-1D. According to an embodiment, the expansion and/or contraction of the nano-scale protrusions 104 may be tuned to identify the morphologies of the nano-scale protrusions 104 that result in the substantially highest Raman intensity for a SERS apparatus. In this regard, a single SERS-active apparatus 100 may be employed instead of requiring that a number of apparatuses having different morphologies be fabricated to make this determination.

The deformable layer 102 and the nano-scale protrusions 104 may be formed through any suitable process. By way of example, a mold of the nano-scale protrusions 104 may be formed, for instance, of silicon, and a body and curing agent of a flexible polymer, such as, PDMS, is poured over the silicon mold and left to cure. In this example, the flexible polymer poured onto the silicon mold may be used as an intermediate mold and another set of a body and curing agent of a flexibly polymer may be poured over the intermediate mold and left to cure. The resulting transferred apparatus will have the same pattern as the silicon mold.

As other examples, the deformable layer 102 and the nano-scale protrusions 104 are formed using a Bosch etching process, a nanoimprinting process by physical vapor deposition, by surface atom migration, etched back by reactive etching with or without a lithographically defined masking pattern, embossing, or a combination of those processes, etc.

Figure 2:
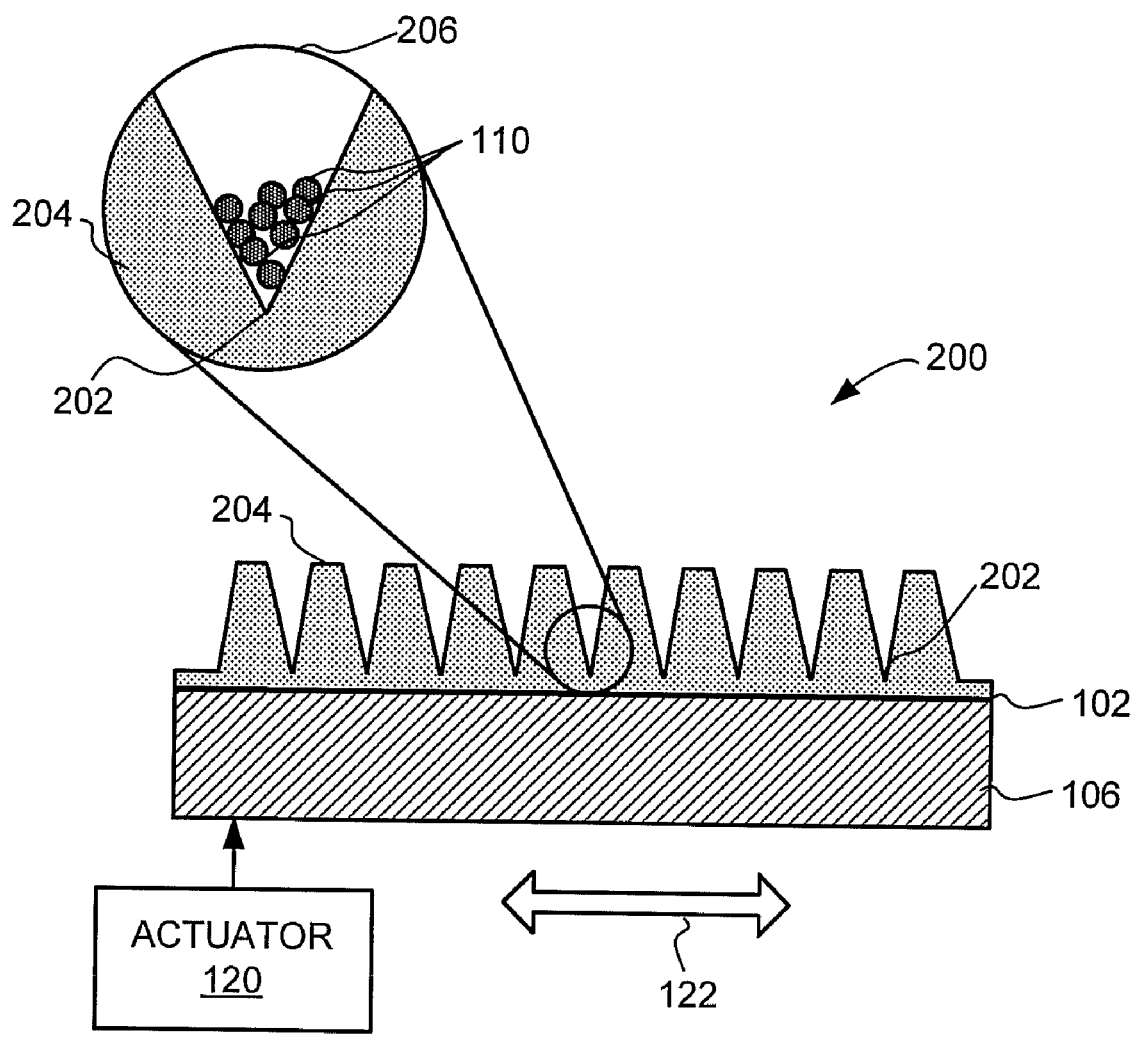
FIG. 2 shows a cross-sectional side view of a tunable SERS-active apparatus, according to another embodiment of the invention.

With reference now to FIG. 2, there is shown a cross-sectional side view of a tunable SERS-active apparatus 200 configured in accordance with another embodiment of the present invention. The apparatus 200 depicted in FIG. 2 includes all of the features as the apparatus 100 depicted in FIG. 1B, except that the bases of the nano-scale protrusions 204 form valleys 202. As shown in FIG. 2, SERS-active nanoparticles 110 are disposed near the bases, in the valleys 202, of the nano-scale protrusions 204.

The morphologies of the nano-scale protrusions 204 are configured to change in response to expansion and/or contraction of the deformable layer 102 and the nano-scale protrusions 204. In this regard, the angles of the nano-scale protrusions 204 at their respective bases and the distances between the valleys 202 are configured to be varied as the deformable layer 102 and the nano-scale protrusions 204 are either compressed or expanded.

Figure 3A:
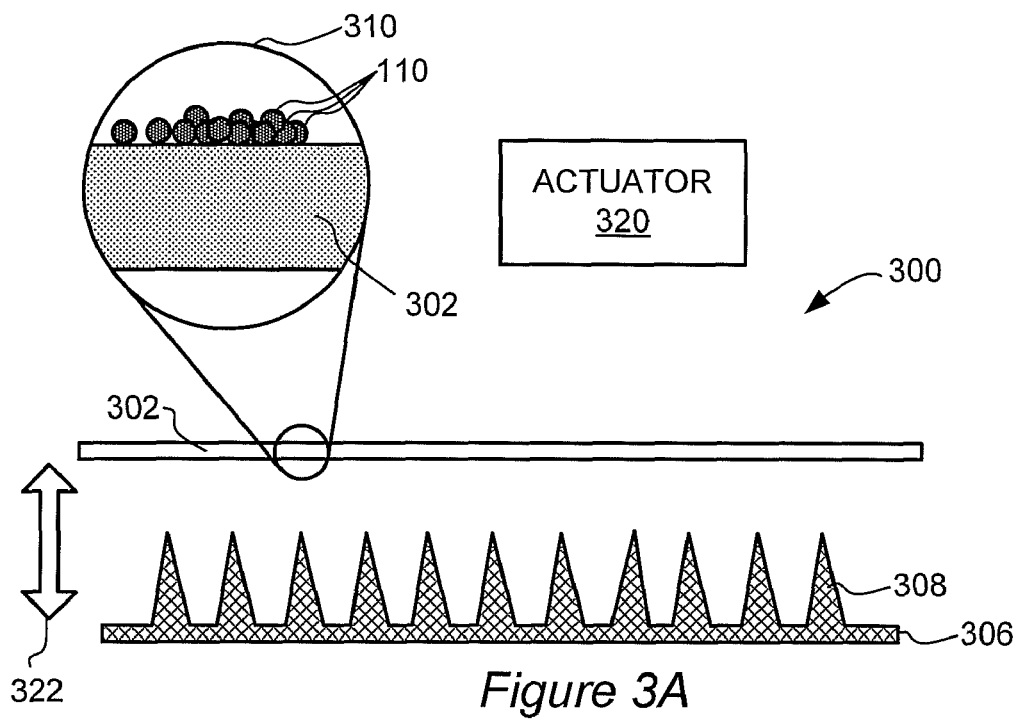
FIGS. 3A-3C, respectively, show cross-sectional views of a SERS-active apparatus during three different levels of deformation in a deformable layer, according to an embodiment of the invention.
Figure 3B:
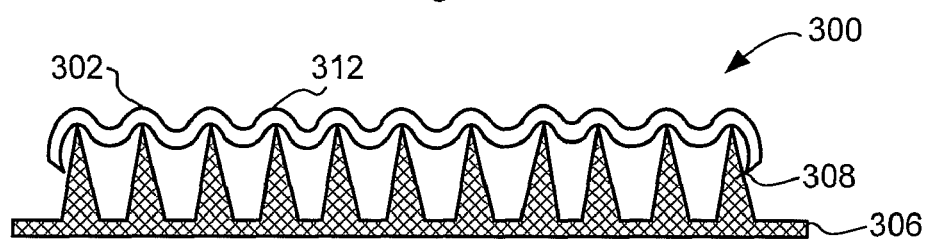
Figure 3C:
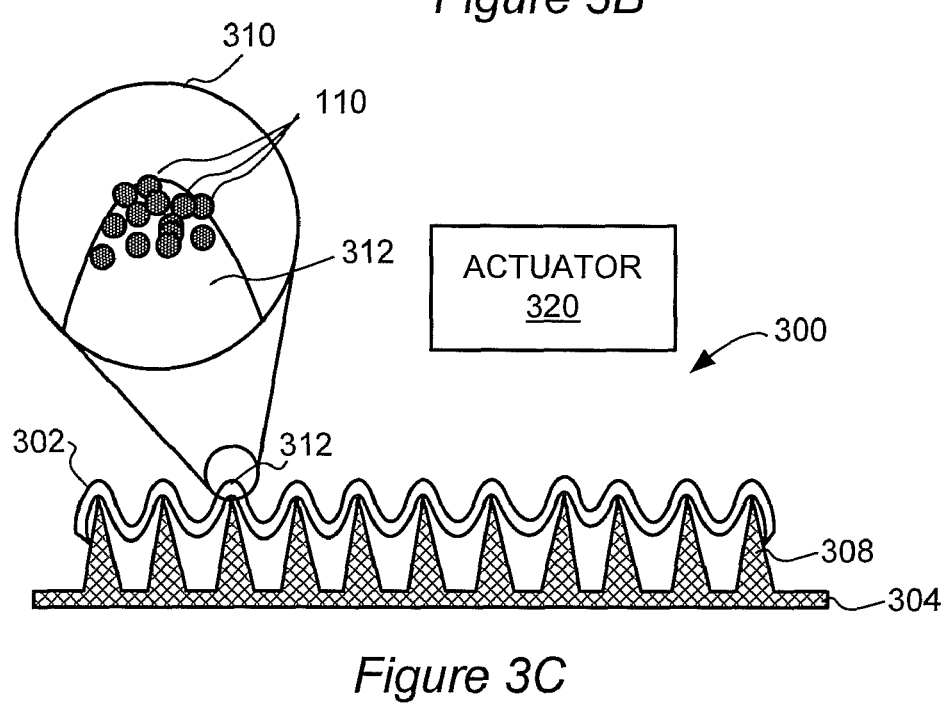

Turning now to FIGS. 3A-3C, there are shown cross-sectional side views of a SERS-active apparatus 300 during three different levels of deformation in a deformable layer 302 configured in accordance with another embodiment of the present invention. As shown in FIG. 3A, the apparatus includes a deformable layer 302 and a substrate 306 having a plurality of nano-scale projections 308 extending from a surface of the substrate 306. The deformable layer 302 may be composed of any of the flexible materials discussed above with respect to the deformable layer 102 above. In addition, the substrate 306 may be composed of any of the materials discussed above with respect to the substrate 106 above.

However, in contrast to the substrate 106 discussed above with respect to FIG. 1A, the substrate 306 depicted in FIGS. 3A-3C includes a plurality of nano-scale projections 308. The nano-scale projections 308 may be arranged similarly to the manner in which the nano-scale protrusions 104 have been depicted in and discussed above with respect to FIG. 1A. In addition, although the nano-scale projections 308 have been depicted as having conical shapes, the nano-scale projections 308 may be shaped as, pillars, pyramids, hemispheres, etc., or have amorphous shapes without departing from a scope of the apparatus 300. According to a particular example, the heights of the nano-scale protrusions 104 are about 1 micron and the distances between the tips of the nano-scale projections 308 are between about 100 nm to 500 nm. In another example, the distances between the tips of the nano-scale projections 308 are sub-wavelength. In another example, the distances are in a range of wavelength to sub-wavelength.

As further shown in FIG. 3A, an actuator 320 is provided to control the relative positions, as denoted by the arrow 322, of the deforming layer 302 and the substrate 306. In one example, the actuator 320 may comprise a mechanical device, such as, an encoder capable of sub-micron or micron level movement. In this example, the actuator 320 is configured to change the position of either or both of the deforming layer 302 and the substrate 306 to cause the deformable layer 302 and the substrate 306 to contact each other. The actuator 320 may continue to press the nano-scale projections 308 into the deformable layer 302 to cause the deformable layer 302 to obtain the shapes of the nano-scale projections 308, as shown in FIGS. 3B and 3C.

In another example, the actuator 320 may comprise a mechanical device, such as, a fan or blower configured to controllably remove a fluid, such as, air, water, or other fluid, from the spaces between the nano-scale projections 308 to cause the deformable layer 302 to obtain the shapes of the nano-scale projections 308. In a further example, the actuator 320 may comprise a fan or blower configured to controllably insert a fluid, such as, air, water, or other fluid, into the spaces between the nano-scale projections 308 to cause the deformable layer 302 to obtain rounded, bubble-like, sections above the spaces between the nano-scale projections 308.

In comparing FIGS. 3B and 3C, the deformable layer 302 shown in FIG. 3B includes a plurality of nano-scale protrusions 312 having a first curvature and the nano-scale protrusions 312 shown in FIG. 3C have a second curvature. Similar types of nano-scale protrusions 312 having various curvatures may also be formed through application of a fluid into the spaces between the nano-projections 308 as discussed above. In any regard, by controlling the degree to which the nano-projections 308 are pushed into the deformable layer 302 or the amount of fluid either removed from or inserted between the deformable layer 302 and the nano-projections 308, the curvatures of the protrusions 312 may be varied to thereby identify the morphologies of the protrusions 312 that result in the substantially highest Raman intensity for a SERS apparatus. According to an embodiment, the deformable layer 302 is configured to substantially return to its original shape, for instance, as shown in FIG. 3A, following removal of the interaction on the deformable layer 302 caused by the actuator 320.

In addition, a location on the deformable layer 302 and an end of a protrusion 312 are depicted in the enlargements 310 shown in FIGS. 3A and 3B. As shown in the enlargements 310, a plurality of SERS-active nanoparticles 110 are disposed on the outer surface at various locations (protrusions 312) corresponding to the locations of the nano-scale projections 308. Note that embodiments of the present invention are not limited to nanoparticles 110 disposed over those locations on the deformable layer 302. In other embodiments, the nanoparticles 110 may be disposed over nearly the entire surface of the deformable layer 302.

Figure 4:
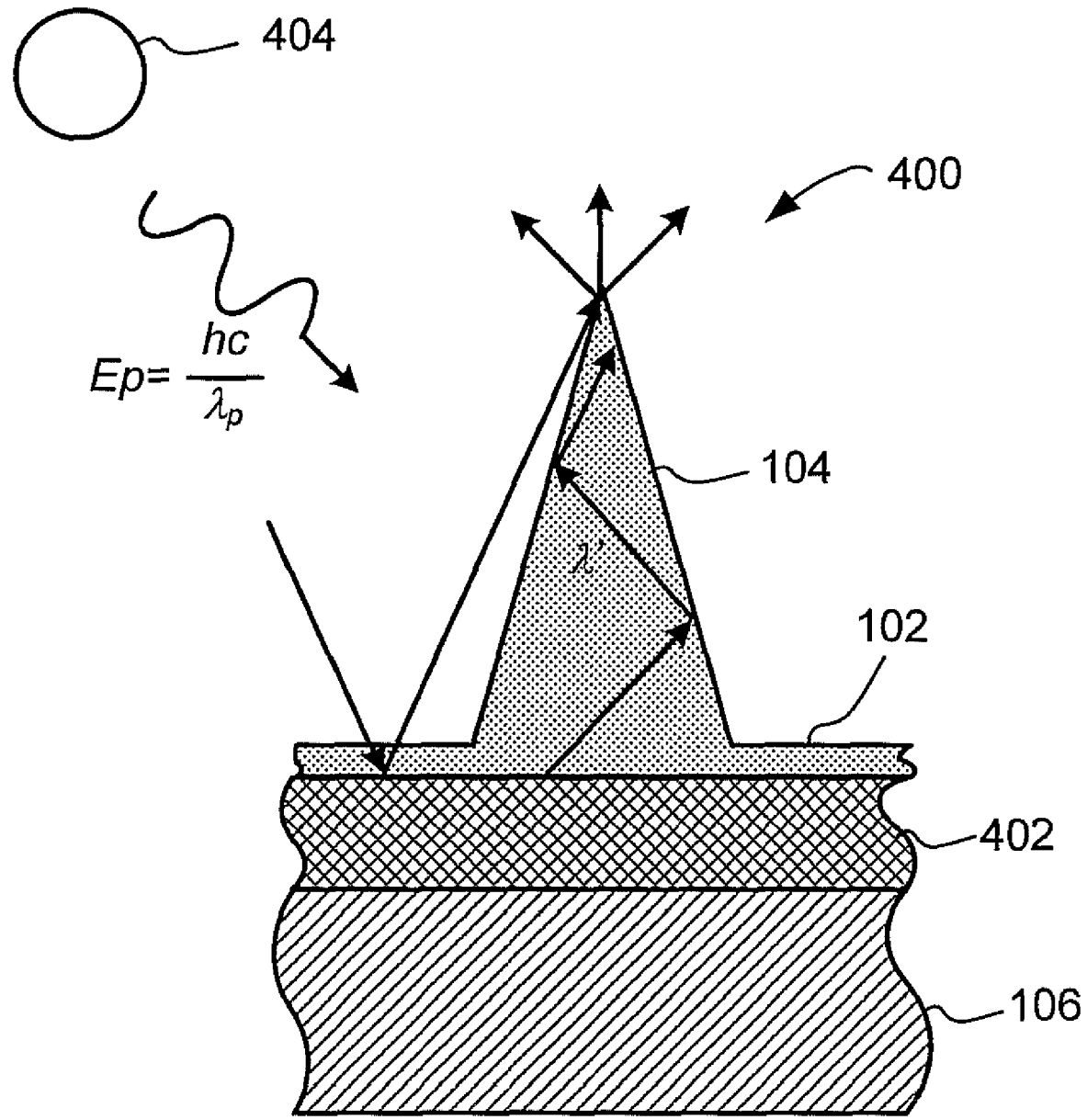
FIG. 4 shows a cross-sectional view of a portion of the SERS-active apparatus depicted in FIGS. 1A and 1B, according to an embodiment of the invention.

Turning now FIG. 4, there is shown a cross-sectional view of a portion of the SERS-active apparatus 100 depicted in FIGS. 1A and 1B, according to embodiments of the invention. The apparatus 400 depicted in the example of FIG. 4 includes all of the features discussed above with respect to the apparatus 100 in the example of FIG. 1A. In addition, however, the apparatus 400 also includes an optional reflective layer 402, which may be composed of a reflective metallic or other type of reflective material and may be fabricated to have a mirror-like functionality. In addition, the reflective layer 402 may be fabricated to have a relatively flat, concave, convex, or amorphous surface. The reflective layer 402 is considered optional because embodiments of the apparatus 400 may be implemented without having the reflective layer 402.

In instances where the apparatus 400 implements the reflective layer 402, similarly to the substrate 106 as discussed above with respect to FIG. 1A, the reflective layer 402 is, in one example, attached to the deformable layer 102. In this example, the reflective layer 402 is also formed of a deformable material and the deformable layer 102 and the reflective layer 402 may be operated to have the same or similar rate of deformation. In another example, the deformable layer 102 is separately movable from the reflective layer 402 and thus may have a different rate of deformation than the reflective layer 402. In this example, the reflective layer 402 is composed of a metallic material or other type of reflective material and may be fabricated to have a mirror-like functionality. In one embodiment, the reflective layer 402, comprises a film of material that is placed on the substrate 106. In another embodiment, the reflective layer 402 is deposited onto the substrate 106, for instance, through chemical vapor deposition, sputtering, etc.

In accordance with one embodiment, the substrate 106 and the reflective layer 402 may be formed as a common layer. In this regard, the substrate 106 may be formed to include either a single reflective surface or the entire substrate 106 may be formed and finished to be reflective. In another embodiment, the reflective layer 402 is disposed on top of the deformable layer 102, substantially between nano-scale protrusions 104.

Although the discussion of FIG. 4 has so far been made with particular reference to the examples depicted and discussed with respect to FIGS. 1A-1D, it should be understood that the discussion presented therein is also applicable to the examples depicted and discussed with respect to FIGS. 2 and 3A-3C. In this regard, the reflective layer 402 may be implemented in any of the examples of the apparatus 100, 200, 300, and 400 discussed herein.

According to embodiments of the invention, the nano-scale protrusions 104, 204, and 312 are formed of a transparent material. The remaining sections of the deformable layer 102 and 302 are also formed of a transparent material. As further shown in FIG. 4, the material for the deformable layer 102 and nano-scale protrusions 104 may be selected to emit Raman scattering light with Raman excitation wavelengths, $\lambda'$, that enhance Raman spectrum of molecules located at or near the SERS-active nanoparticles 110 when the nano-scale protrusions 104 are optically pumped with light of an appropriate pump wavelength $\lambda_p$ from a light source 404. In instances where the reflective layer 402 is provided, the Raman spectrum of molecules located at or near the SERS-active nanoparticles 110 may also be enhanced with light and reflected from the reflective layer 402.

FIG. 4 further shows optically pumping a nano-scale protrusion 104 in accordance with embodiments of the present invention. Although FIG. 4 has been depicted as having the configuration depicted in FIG. 1A, it should clearly be understood that FIG. 2A may instead have the configuration depicted in any of FIGS. 2A and 3A without departing from a scope of the invention. In FIG. 4, the nano-scale protrusion 104 is illuminated with light from a light source 404 having a pump wavelength $\lambda_p$ and corresponding energy $E_p$:

$$E_p = \frac{hc}{\lambda_p}$$

where h is Planck's constant, and c is the speed of light in free space.

The light emitted from the nano-scale protrusion 104 may be trapped by internal reflection within the nano-scale protrusion 104 due to the contrast between the refractive index of the nano-scale protrusion 104 material and the relatively lower refractive index of the surrounding air. As a result, a substantial portion of the emitted light may be reflected off of the interior walls within the nano-scale protrusion 104, directed toward the tip of the nano-scale protrusion 104, and emitted near the tip of the nano-scale protrusion 104, as shown in FIG. 4. In addition, in instances where the reflective layer 402 is implemented, a substantial portion of the emitted light may be reflected off of the reflective layer 402 and directed toward the tip of the nano-scale protrusion 104. The light may constructively interfere to produce amplified light with the Raman excitation wavelengths $\lambda'$ emitted near the tip of the nano-scale protrusion 104.

As discussed above, the morphology of the nano-scale protrusion 104 may be modified through any of the various manners discussed above to vary the emission of the Raman excitation light. In one regard, the nano-scale protrusion 104 morphology may be varied a number of times until a morphology that results in an optimized and/or maximized emission of Raman excitation light is identified.

In other embodiments, the nano-scale protrusions 104 may be configured with one or more light emitters, including quantum wells ("QWs") or light-emitting particles, such as quantum dots ("QDs"), atoms or molecules, that may be selected and dimensioned to emit Raman excitation light with Raman excitation wavelengths $\lambda'$. Various examples of the one or more light emitters that may be provided in the nano-scale protrusions 104 are discussed in detail in the PCT/US2008/083827 and the Ser. No. 12/771,824 applications for patent.

Returning to FIGS. 1A-1D, 2, and 3A-3C, the tunable SERS-active apparatus 100, 200, 300 may be used to identify one or more analyte molecules by selecting the composition of the nano-scale protrusions 104, 204, 312 or light emitters to emit Raman excitation wavelengths $\lambda'$ causing the analytes to produce associated Raman spectra of Raman scattered light. Each Raman spectrum may be detected and used to identify each of the analytes. The SERS-active nanoparticles 110 deposited near the tip of the nano-scale protrusions 104, 312 or the valley 202 of the nano-scale protrusion 204, may be composed of silver ("Ag"), gold ("Au"), copper ("Cu") or another metal suitable for forming a structured metal surface that when illuminated by the Raman excitation wavelengths $\lambda'$ enhances the intensity of the Raman scattered light.

Figure 5:
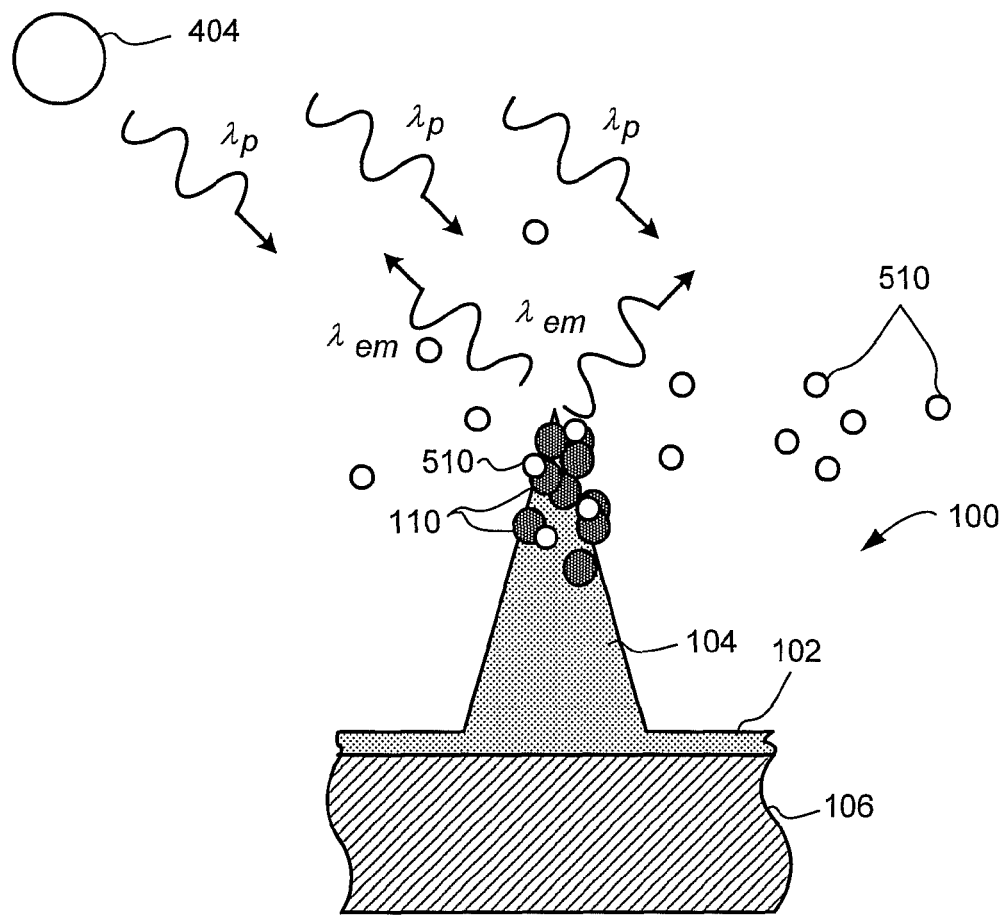
FIG. 5 shows a cross-sectional view of a nano-scale protrusion of an optically pumped SERS-active apparatus, according to an embodiment of the invention.

FIG. 5 shows a cross-sectional view of a nano-scale protrusion 104 of an optically pumped SERS-active apparatus 100 operated in accordance with embodiments of the present invention to produce a Raman spectrum. Although the discussion of FIG. 5 is made with particular reference to the examples depicted and discussed with respect to FIGS. 1A-1D, it should be understood that the discussion presented therein is also applicable to the examples depicted and discussed with respect to FIGS. 2 and 3A-3C. In this regard, the any of the apparatuses 100, 200, 300, and 400 discussed herein may be used in the example discussed with respect to FIG. 5.

As shown in FIG. 5, an analyte 510 is introduced and the nano-scale protrusion 104 is optically pumped with light having a pump wavelength $\lambda p$ that causes the emission of Raman excitation light. Although not shown, a reflective layer 402 may be provided as discussed above with respect to FIG. 4 to increase the amount of light directed toward the end of the nano-scale protrusion 104. The Raman excitation wavelengths cause analytes 510 located near the ends of the nano-scale protrusions 104 to produce a Raman spectrum of Raman scattered light over a range wavelengths denoted by $\lambda em$. The intensity of the Raman scattered light may also be enhanced as a result of a number of mechanisms. The first mechanism is an enhanced electromagnetic field produced at the surface of the SERS-active nanoparticles 110, enhanced Raman intensity through variation of the morphology of the nano-scale protrusions 104, and the materials and thickness of the QWs may also be selected so that the Raman excitation wavelengths $\lambda'$ are close to the plasma wavelength of the nanoparticles 110. As a result, conduction electrons in the metal surfaces of the nanoparticles 110 are excited into an extended surface excited electronic state called a "surface Plasmon polariton." Analytes 510 adsorbed on or in close proximity to the nanoparticles 110 experience a relatively strong electromagnetic field. Molecular vibrational modes directed normal to the nanoparticle 110 surfaces are most strongly enhanced. The intensity of the surface plasmon polariton resonance depends on many factors including the morphology of the nano-scale protrusions 104, the morphology of the nanoparticles 110, and the wavelength of the Raman excitation light $\lambda'$ emitted from the QWs.

The second mode of enhancement, charge transfer, may occur as a result of the formation of a charge-transfer complex between the surfaces of the nanoparticles 110 and the analyte 510 absorbed to these surfaces. The electronic transitions of many charge transfer complexes are typically in the visible range of the electromagnetic spectrum.

Figure 6:
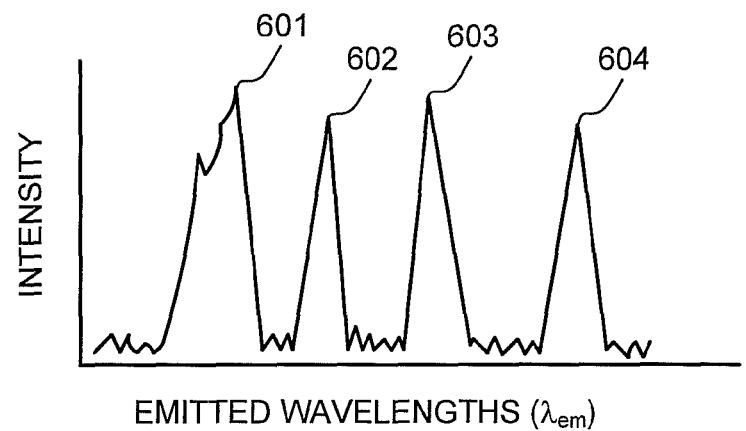
FIG. 6 shows an example Raman spectrum associated with Raman scattered light, according to an embodiment of the invention.

FIG. 6 shows an example Raman spectrum associated with Raman scattered light in accordance with embodiments of the invention. In the example of FIG. 6, the Raman spectrum comprises four intensity peaks 601-604, each peak corresponding to a particular frequency. The intensity peaks 601-604 and associated wavelengths may be used like a finger print to identify the associated analyte 510.

II. Electronically Operated SERS-active Systems

Figure 7A:
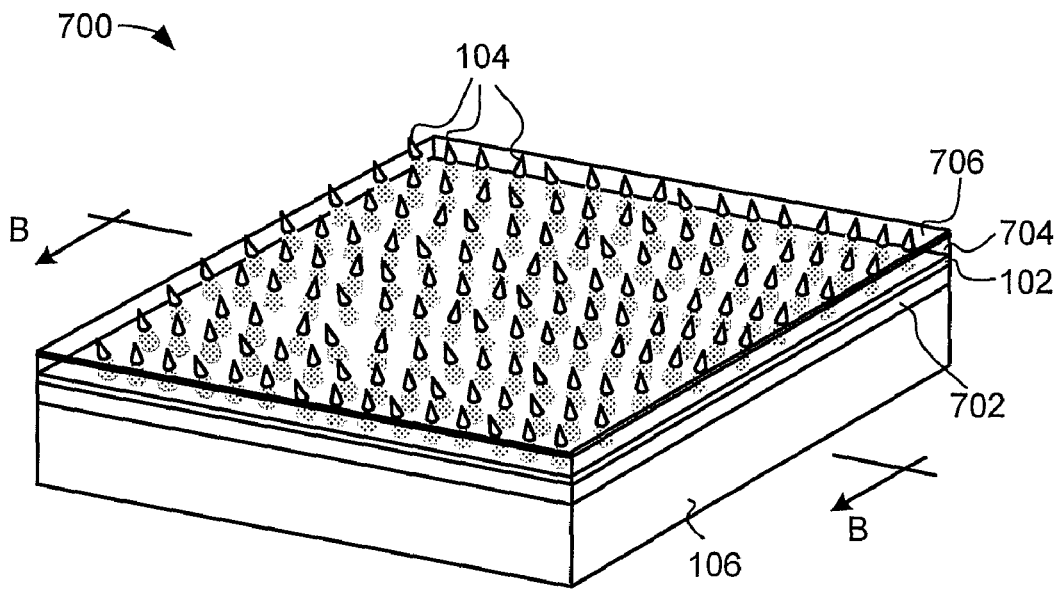
FIG. 7A shows an isometric view of a tunable SERS-active apparatus, according to another embodiment of the invention.

FIG. 7A shows an isometric view of a tunable SERS-active apparatus 700 configured in accordance with embodiments of the present invention. As shown in FIG. 7A, the apparatus 700 includes a deformable layer 102 that includes a plurality of nano-scale protrusions 104, similarly to the apparatus 100 depicted in FIGS. 1A-1D. The apparatus 700 also includes a first electrode layer 702 disposed on the substrate 106, a dielectric layer 704 disposed above the first electrode layer 702, and a second electrode layer 706 disposed on the dielectric layer 704.

As shown, the nano-scale protrusions 104 and the deformable layer 102 are disposed on the first electrode layer 702. In addition, the nano-scale protrusions 104 are embedded within the dielectric layer 704 with the ends, or tips, thereof extending above the second electrode layer 706. As shown in the example of FIG. 7A, the ends of the nano-scale protrusions 104 are directed away from the substrate 106.

Figure 7B:
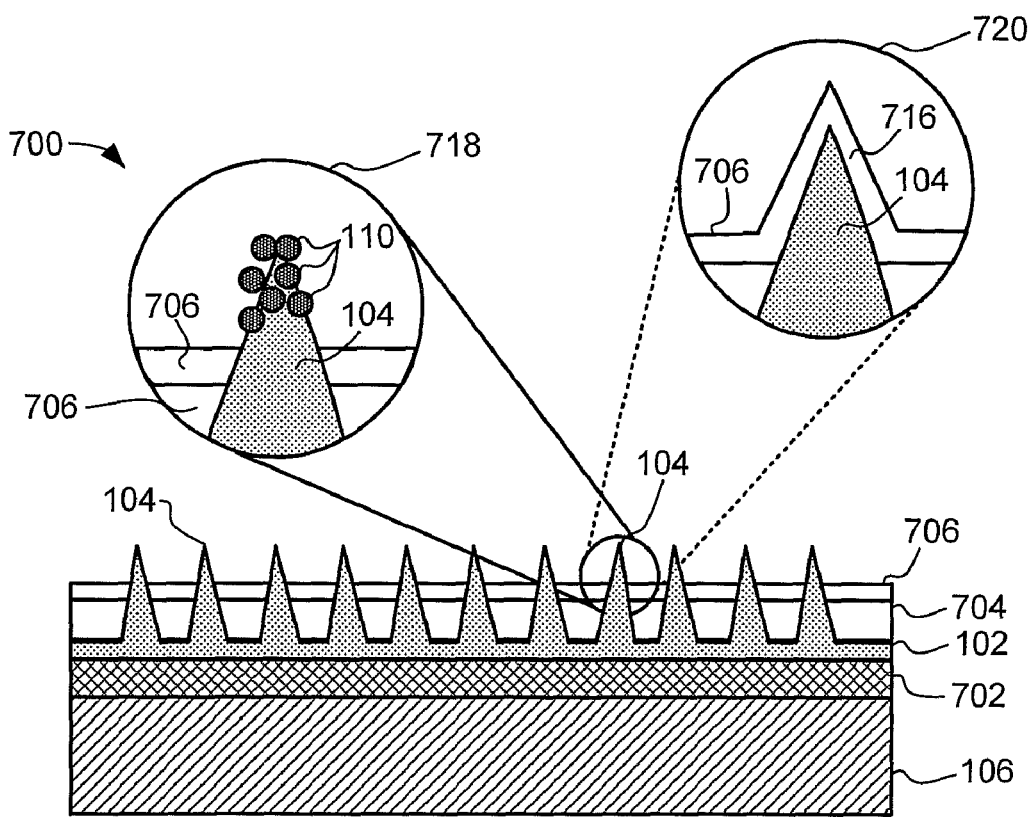
FIG. 7B shows a cross-sectional view of the SERS-active apparatus along a line B-B in FIG. 7A, according to an embodiment of the invention.

FIG. 7B shows a cross-sectional view along a line B-B, shown in FIG. 7A, of the SERS-active apparatus 700 in accordance with embodiments of the present invention. As shown in the enlargement 718, the SERS-active nanoparticles 110 are provided on the nano-scale protrusions 104, similarly to FIG. 1B. FIG. 7B also shows an enlargement 720 of the nano-scale protrusion 104, which represents a second embodiment where, rather than coating the tips of the nano-scale protrusions 104 with SERS-active nanoparticles, a thin portion 716 of the second electrode layer 708 covers at least a portion of the nano-scale protrusion 104 tip.

In the embodiment depicted in FIGS. 7A and 7B, the morphologies of at least the deformable layer 102 and the nano-scale protrusions 104 are configured to be varied as discussed above. In this regard, and according to an embodiment, one or more of the first electrode 702, the dielectric layer 704, and the second electrode 706 are also formed of a flexible material to thus enable the nano-scale protrusions 104 to move. In another embodiment, however, the dielectric layer 704 and/or the second electrode 706 may be fabricated with gaps, such as, as a mesh structure, to provide sufficient space for the morphologies of the nano-scale protrusions 104 to be varied. In this embodiment, the deformable layer 102 may be detached from the first electrode 702.

In any regard, the first electrode 702 may be formed on the substrate 106 using any suitable formation process, such as, CVD, wafer bonding, sputtering, etc. In addition, the first electrode 702 may be a blank or patterned. The deformable layer 102 and the nano-scale protrusions 104 may be formed through any of the techniques described above with reference to FIGS. 1A and 1B. The dielectric layer 704 may be composed of glass, $SiO_2$, $Al_2O_3$, or any other suitable transparent dielectric material and may be formed around the nano-scale protrusions 104 using a spin-on-glass technique. The second electrode layer 706 may be formed on the dielectric layer 704 using CVD and etched away around the nanowires so that SERS-active nanoparticles 110 may be deposited using CVD, as shown in the enlargement 718 in FIG. 7B, or, in another embodiment, the second electrode layer 706 may remain leaving a thin layer of conductive material on the tips of the nano-scale protrusions 104, as shown in the enlargement 720 in FIG. 7B.

The tapered nanowires of the SERS-active apparatus 700 may also be configured as pn or p-i-n junctions and electronically pumped to generate Raman excitation light as discussed in detail in the PCT/US2009/052308 application for patent.

Figure 8:
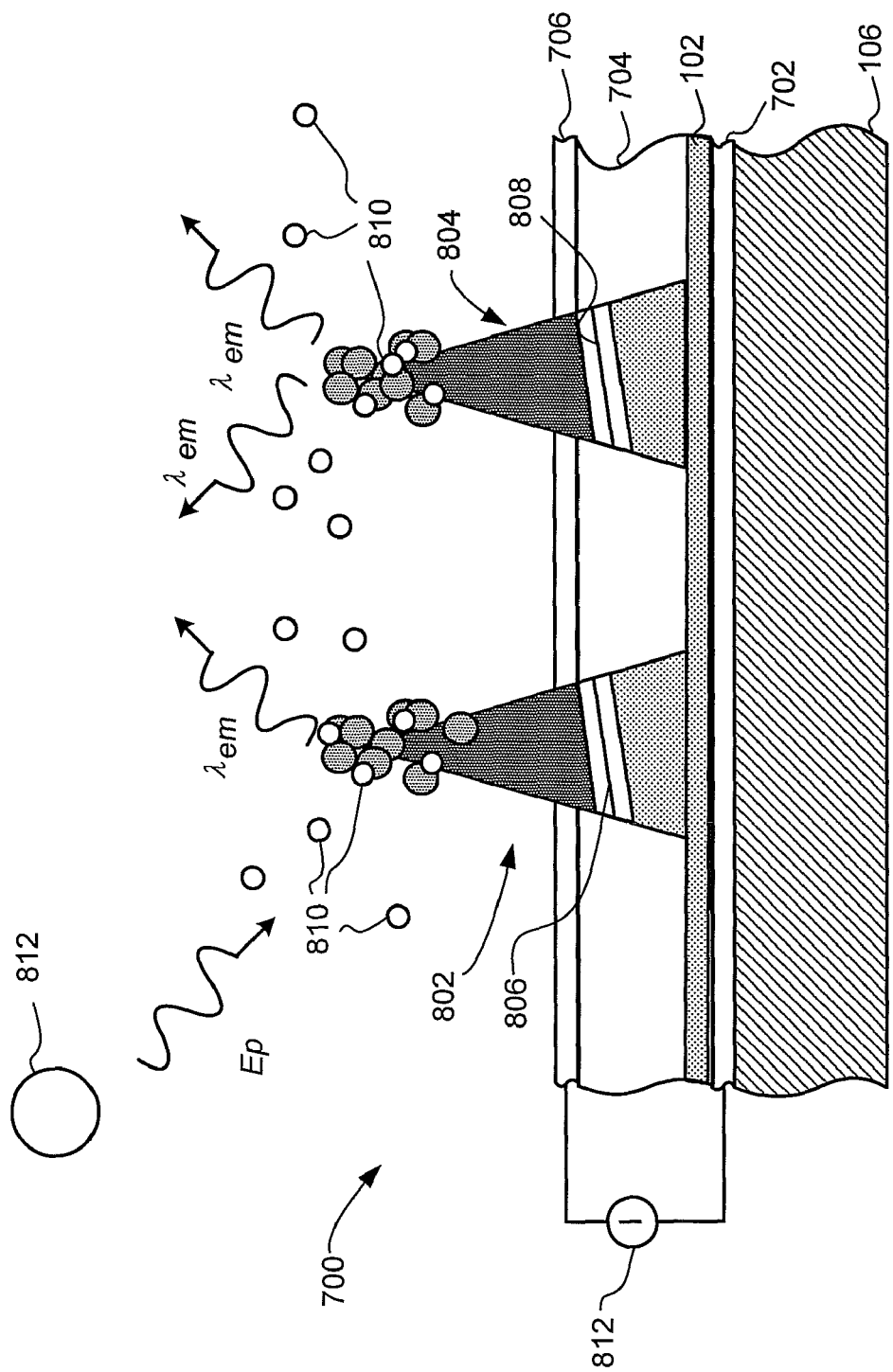
FIG. 8 shows a cross-sectional view of two nano-scale protrusions of an electronically operated SERS-active apparatus, according to an embodiment of the invention.

FIG. 8 shows a cross-sectional view of two nano-scale protrusions 802 and 804 of an electronically operated SERS-active apparatus 700 in accordance with embodiments of the present invention to produce a Raman spectrum. The nano-scale protrusions 802 and 804 are each configured with a single QW 806 and 808, respectively, as described above with reference to PCT/US20081083827 application for patent. As shown in FIG. 8, an analyte 810 is introduced and the nano-scale protrusions 802 and 804 are electronically pumped by a voltage source 812 that causes the emission of Raman excitation light with Raman excitation wavelengths from the layers 806 and 808. As described above with reference to FIG. 4, the light is directed toward the tips of the nano-scale protrusions 802 and 804. In addition, the light is substantially confined within, and emitted near the tips of, the nano-scale protrusions 802 and 804. As also discussed above, the morphologies of the nano-scale protrusions 802 and 804 are varied, which varies the characteristics of the light emitted near the tips of the nano-scale protrusions 802 and 804.

The Raman excitation wavelengths cause analytes 810 located near the tips of the nano-scale protrusions 802 and 804 to produce a Raman spectrum of Raman scattered light over a range of emission wavelengths $\lambda_{em}$. The intensity of the Raman scattered light may also be enhanced as a result of surface plasmon polaritons formed on the nanoparticles 810, or charge transfer, as described above with reference to FIG. 5, producing an enhanced Raman spectrum, such as the Raman spectrum shown in FIG. 6.

III. Analyte Sensors and Detectors

Figure 9A:
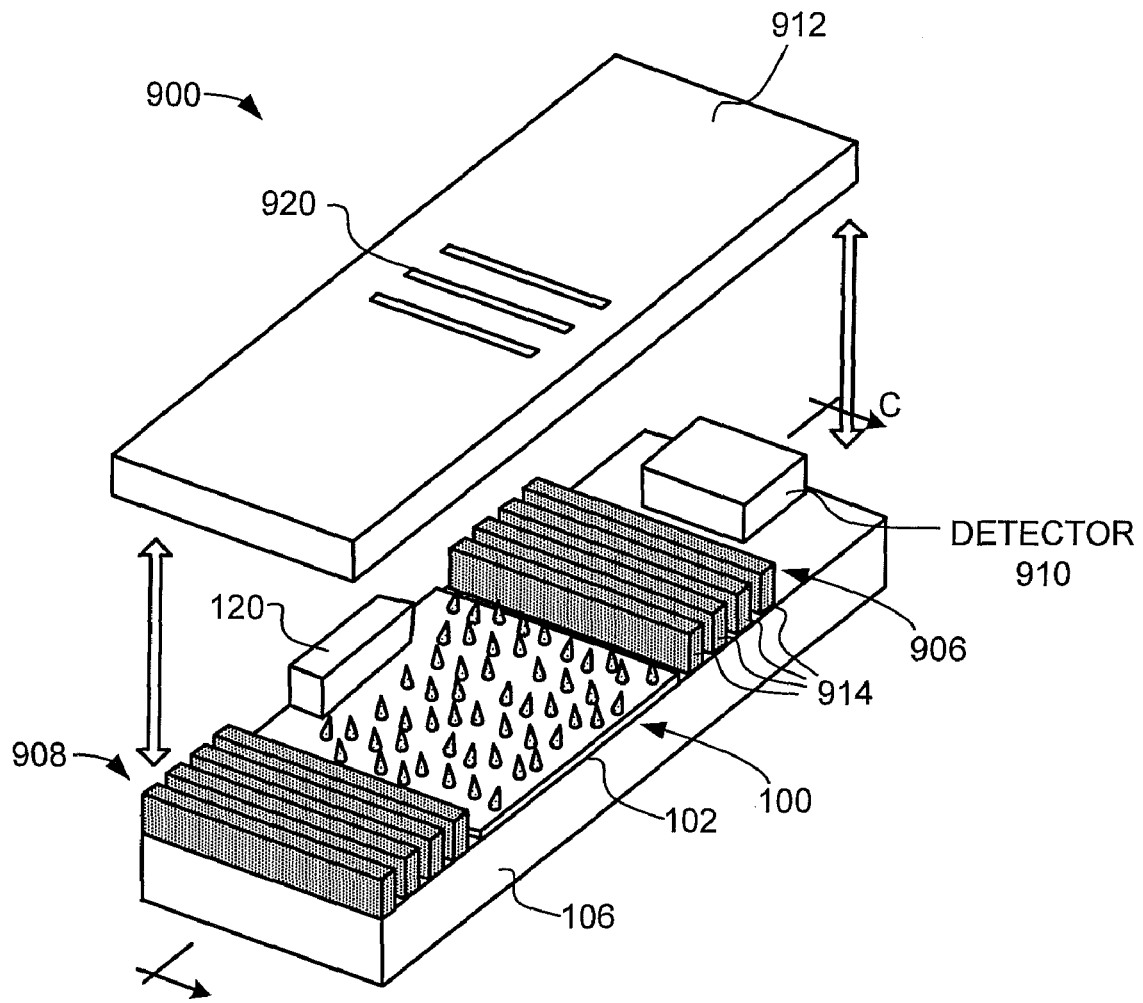
FIG. 9A shows an exploded isometric view and schematic representation of an analyte sensor, according to an embodiment of the invention.

FIG. 9A shows an exploded isometric view and schematic representation of an analyte sensor 900 configured in accordance with embodiments of the present invention. The sensor 900 includes a SERS-active apparatus 100, which includes a deformable layer 102 and a substrate 106, which may also be deformable, for instance, as shown in FIGS. 1A and 1B. As shown in FIG. 9A, the SERS-active apparatus 100 is located between a first reflector 906 and a second reflector 908. The sensor 900 also includes a detector 910, such as a photodetector, disposed on the substrate 106 and a cover 912. The SERS-active apparatus 100 may be an optically pumped system, such as the apparatus 100 described above with reference to FIG. 1A.

Figure 9B:
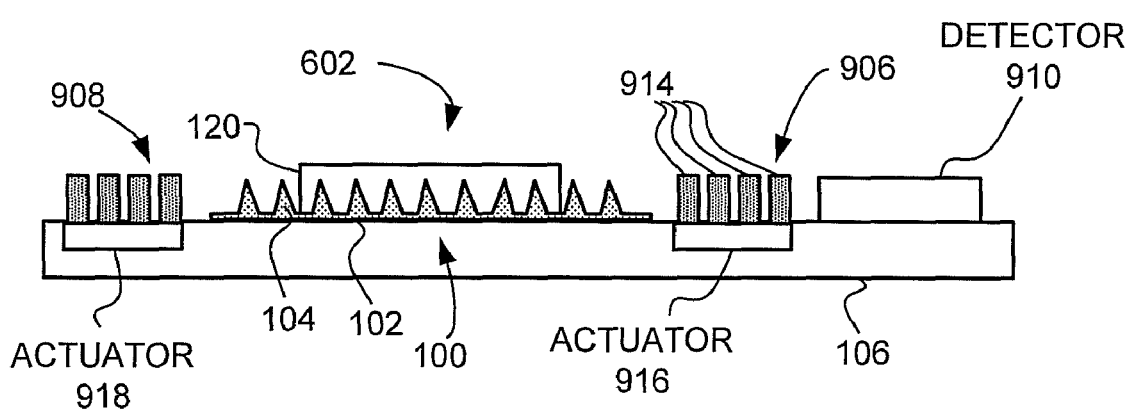
FIG. 9B shows a cross-sectional view of the substrate portion of the sensor along a line C-C in FIG. 9A, according to an embodiment of the invention.

FIG. 9B shows a cross-sectional view of the substrate 106 portion of the sensor 900 along a line C-C, shown in FIG. 9A, in accordance with embodiments of the present invention. As shown in FIG. 9B, the reflectors 906 and 908 are each composed of thin layers of dielectric material separated by air, such as thin layers 914. Appropriate selections of thin layer material, layer thickness, and layer spacing enable the reflectors 906 and 908 to be operated with a specified reflectivity for different wavelengths of light. FIG. 9B also reveals that the reflectors 906 and 908 are mechanically coupled to actuators 916 and 918, respectively. The actuators 916 and 918 may be separately operated to selectively adjust and tune the reflectivity of the reflectors 906 and 908 by controlling the separation distance between the thin layers. The separation distance may be controlled to produce ultra-high reflectivity mirrors of 99% or better over a narrow range of wavelengths, or the reflectors 906 and 08 may be tuned to reflect a broad spectrum of light.

The sensor 900 is operated by introducing an analyte to the nanowires of the SERS-active apparatus 100. This may be accomplished by allowing an analyte in the gas phase to pass through ventilation holes 920 formed in the cover 912, as shown in FIG. 9A. In other embodiments, the analyte may be injected into the region between the SERS-active apparatus 100 and the cover 912. In certain embodiments, when the SERS-active apparatus 100 is configured to be operated as an optically pumped SERS-active apparatus 100, the nano-scale protrusions are illuminated by light with an appropriate pump wavelength, as described above with reference to FIG. 5. The reflector 908 may be tuned to operate as a nearly fully reflective mirror for the wavelengths of light emitted from the analyte, and the reflector 906 may be tuned to operate a partially reflective mirror for the same wavelengths. As a result, the light emitted from the analyte resonates between the reflector 906 and 908, builds-up, and a portion the light eventually passes through the reflector 9606 and is detected by the detector 910.

Also shown in FIGS. 9A and 9B is an actuator 120 configured to vary the morphology of the deformable layer 102 and the nano-scale protrusions 104. The position of the actuator 120 with respect to the SERS-active apparatus 100 is merely for illustration and should thus not be construed as limiting the invention in any respect. As such, for instance, the actuator 120 may comprise a completely separate component from the sensor 900. In any regard, and as discussed above with respect to FIG. 1B, the actuator may interact with the deformable layer 102 and/or the substrate 106 through one or more of mechanical, electrical, thermal, and/or chemical, interactions to vary the morphologies of the nano-scale protrusions 104. In one respect, the morphologies of the nano-scale protrusions 104 may thus be tuned to cause an optimized and/or maximized Raman light intensity to be generated.

Figure 10:
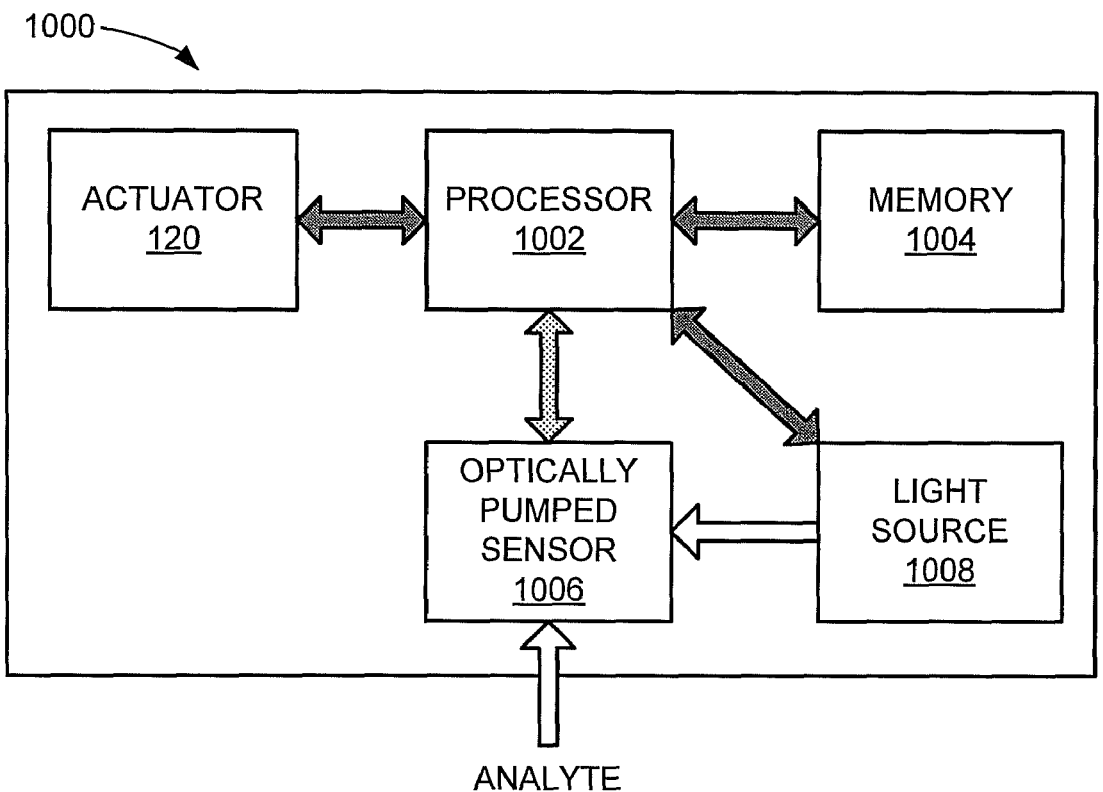
FIGS. 10 and 11, respectively show schematic representations of analyte detector ASICs, according to embodiments of the invention.

The sensor 900 may be implemented as a component of an application specific integrated circuit ("ASIC") configured to operate as an analyte detector. FIG. 10 shows a schematic representation of an analyte detector ASIC 1000 configured in accordance with embodiments of the present invention. The detector 1000 includes a processor 1002, memory 1004, an optically pumped sensor 1006, a light source 1008, and an actuator 120 for varying the morphologies of the nano-scale protrusions 104. The processor 1002 is in electronic communication with the memory 1004, the sensor 1006, the light source 1008, and the actuator 120. The memory 1004 may be flash memory that stores computer readable instructions for operating the light source 1008 and the actuator 120 and stores the information retrieved from the sensor 1006. The light source 1008 is configured to emit light directed toward to the sensor 1006 with wavelengths that pump the nano-scale protrusions 104 of the sensor 1006 as described above with reference to FIG. 5. The processor 1002 operates the reflectors of the sensor 1006 as described above with reference to FIGS. 9A and 9B, receives the Raman spectra results, and may store the results in memory 1004. The processor 1002 also operates the actuator 120 to vary the morphologies of the nano-scale protrusions 104 during a number of iterations to determine which morphology produces the desired Raman spectra results.

Figure 11:
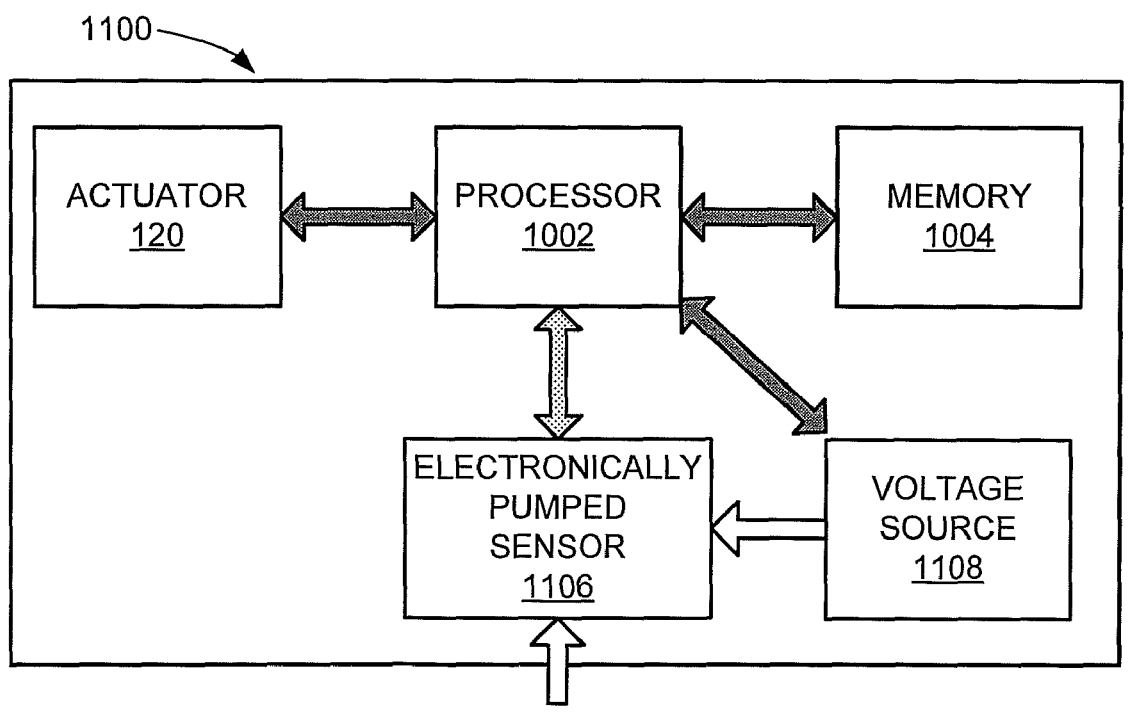

FIG. 11 shows a schematic representation of a second analyte detector ASIC 1100 configured in accordance with embodiments of the present invention. The detector 1100 depicted in FIG. 11 includes all of the features of the detector 1000 depicted in FIG. 10, except that the detector 1100 includes a voltage source 1108 instead of a light source 1008 and an electronically pumped sensor 1106 instead of an optically pumped sensor 1006.

The processor 1002 operates the voltage source 1108 to apply the appropriate voltage to the SERS-active apparatus 100, operates the reflectors of the sensor 1106 as described above with reference to FIG. 10, receives the Raman spectra results, and stores the results in memory 1404. The processor 1002 also operates the actuator 120 to vary the morphologies of the nano-scale protrusions 104 during a number of iterations to determine which morphology produces the desired Raman spectra results.

Figure 12:
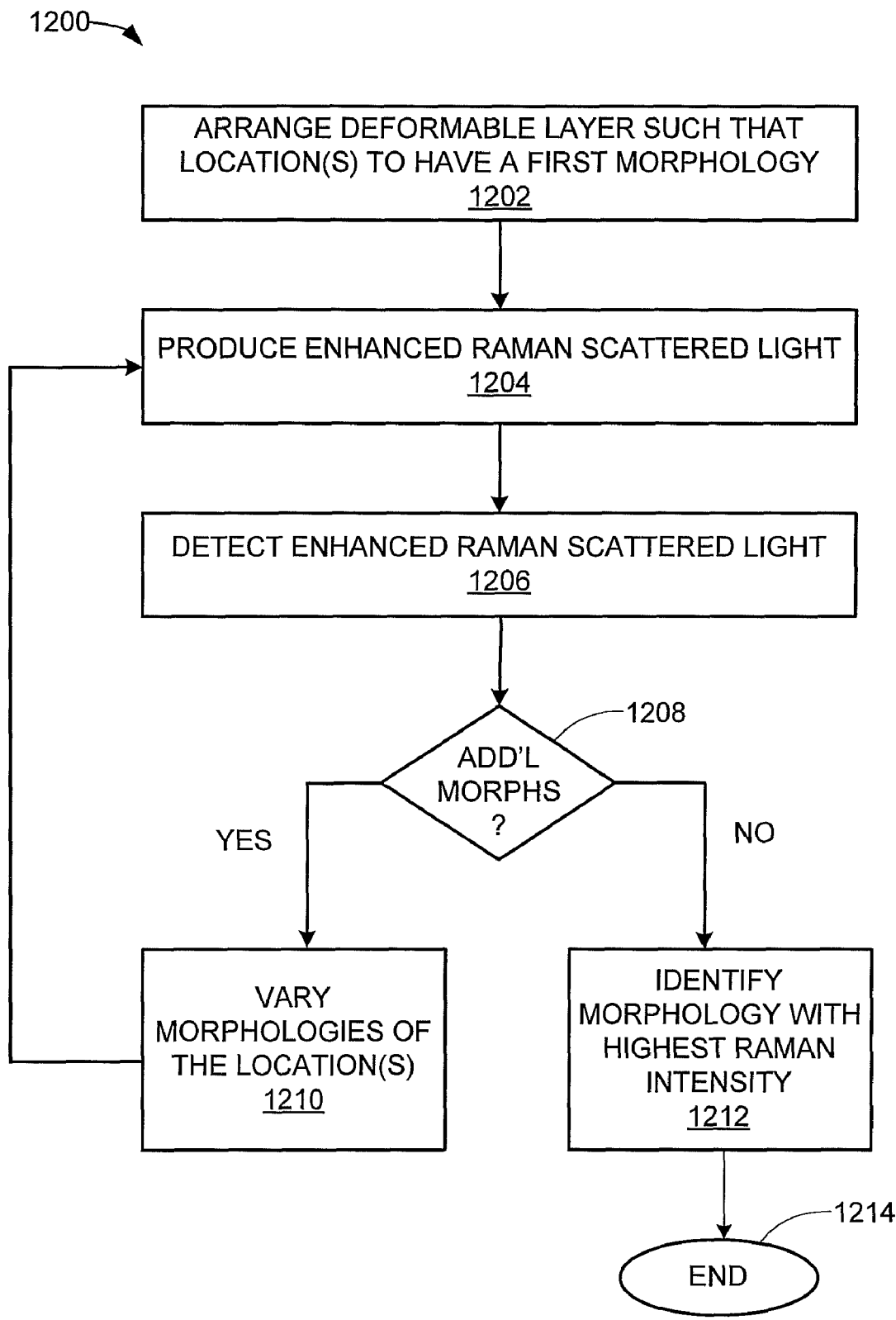
FIG. 12 shows a flow diagram of a method for performing Surface Enhanced Raman Spectroscopy (SERS) on a SERS-active apparatus having a deformable layer and a plurality of nanoparticles disposed at one or more locations on the deformable layer, according to an embodiment of the invention.

With reference now to FIG. 12, there is shown a flow diagram of a method 1200 for performing Surface Enhanced Raman Spectroscopy (SERS) on a SERS-active apparatus 100 having a deformable layer 102 and a plurality of SERS-active nanoparticles 110 disposed at one or more locations on the deformable layer 102, in accordance with embodiments of the present invention. It should be understood that the method 1200 depicted in FIG. 12 may include additional steps and that some of the steps described herein may be removed and/or modified without departing from a scope of the method 1200.

At step 1202, the deformable layer 102 is arranged such that the one or more locations on the deformable layer 102 have a first morphology. The one or more locations may comprise any of the nano-scale protrusions 104 and 312 depicted in FIGS. 1A, 1B, and 3A-3C. In addition, the one or more locations may comprise any of the valleys 202 depicted in FIG. 2. In any regard, the arrangement of the deformable layer 102 at step 1202 may comprise an initial or default state of the deformable layer 102. As such, for instance, at step 1202, the processor 1002 may not cause the actuator 120 to be implemented.

At step 1204, the one or more locations of the deformable layer 102 are illuminated with light of a pump wavelength to cause Raman excitation light to interact with the nanoparticles 110 and produce a first enhanced Raman scattered light from molecules located in close proximity to the nanoparticles 110. As discussed above with respect to FIGS. 10 and 11, the light may be generated by a light source 1008 or through application of a voltage onto the nano-scale protrusions 102 from a voltage source 1108. In addition, at step 1206, the enhanced Raman scattered light may be detected, for instance, by an optically pumped sensor 1006 or an electronically pumped sensor 1106. Moreover, the detected enhanced Raman scattered light may be stored in the memory 1004.

At step 1208, a determination as to whether one or more additional morphologies of the nano-scale protrusions 104 are to be tested is made. This determination may be based upon whether a predetermined number of iterations have been performed, a predetermined amount of time has elapsed, all of the possible morphologies have been tested, etc.

If a determination that one or more additional morphologies are to be tested at step 1208, the morphologies of the one or more locations of the deformable layer 102 are varied, as indicated at step 1210. More particularly, and as discussed above, the processor 1002 may control the actuator 120 to interact with the deformable layer 102 and thereby vary the morphologies of the one or more locations as discussed above with respect to FIGS. 1A-1C, 2, and 3A-3C.

In addition, steps 1204 and 1206 may be repeated to detect and store the Raman scattered light resulting from the varied morphologies. Steps 1204-1210 may be repeated until additional morphologies are not to be tested at step 1208.

Following the "no" condition at step 1208, the processor 1002 may identify the morphology or the actuator 120 setting that resulted in the highest Raman intensity and/or the most accurate test results, as indicated at step 1212. More particularly, for instance, the processor 1002 may analyze the stored Raman scattered light resulting from the different actuator 120 settings to determine which of the results is the most accurate. In addition, at step 1214, the method 1200 may end.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purposes of illustration and description. They are not intended to be exhaustive of or to limit the invention to the precise forms disclosed.

Obviously, many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. A tunable apparatus for performing Surface Enhanced Raman Spectroscopy (SERS), said apparatus comprising:
    a deformable layer comprising a plurality of nano-scale protrusions extending from a plane of the deformable layer, wherein the nano-scale protrusions are spaced apart from each other;
    a plurality of SERS-active nanoparticles disposed on the plurality of nano-scale protrusions, wherein the plurality of SERS-active nanoparticles are to be illuminated with light of a pump wavelength to cause Raman excitation light to interact with the nanoparticles and produce enhanced Raman scattered light from molecules located in close proximity to the nanoparticles; and
    wherein morphologies of the deformable layer and the plurality of nano-scale protrusions are to be varied to modify an intensity of the Raman scattered light produced from the molecules.

2. The apparatus according to claim 1, wherein the deformable layer is composed of a material whose morphology is to be varied upon receipt of at least one of a mechanical, electrical, thermal, and chemical interaction.

3. The apparatus according to claim 1, wherein each of the plurality of nano-scale protrusions comprises a base and a free end, wherein the base is relatively larger than the free end.

4. The apparatus according to claim 3, wherein each of the plurality of nano-scale protrusions comprises a tapered structure coming to a relatively sharp point at the free end.

5. The apparatus according to claim 1, wherein the deformable layer comprises a flexible material and is to be at least one of compressed and expanded, and wherein compression or expansion of the deformable layer varies the morphologies of the plurality of nano-scale protrusions.

6. The apparatus according to claim 1, further comprising:
    a reflective layer positioned to reflect light toward the plurality of nano-scale protrusions on the deformable layer containing the plurality of SERS-active nanoparticles.

7. The apparatus according to claim 1, further comprising:
    a substrate having a plurality of nano-scale projections extending from a plane of the substrate and in a direction toward the deformable layer, wherein the plurality of nano-scale projections are spaced apart from each other; and
    wherein the plurality of nano-scale protrusions are formed in the deformable layer through contact by the plurality of nano-scale projections onto the deformable layer.

8. The apparatus according to claim 7, wherein the morphologies of the plurality of nano-scale protrusions are varied through varying a level of contact between the plurality of nano-scale projections and the deformable layer.

9. The apparatus according to claim 1, wherein the deformable layer comprises at least one quantum well, said apparatus further comprising:
   a first electrode; and
   a second electrode, wherein the quantum well is positioned between the first electrode and the second electrode and is to generate light to pump the deformable layer.

10. The apparatus according to claim 1, wherein the deformable layer comprises a transparent material.

11. The apparatus according to claim 1, further comprising:
   an actuator for varying the morphology of the deformable layer.

12. The apparatus according to claim 1, wherein the plurality of nanoparticles comprises one or more materials selected from a list consisting essentially of: silver, gold, copper and platinum.

13. An analyte sensor comprising:
   a tunable apparatus for performing Surface Enhanced Raman Spectroscopy (SERS), said apparatus comprising,
      a deformable layer comprising a plurality of nano-scale protrusions extending from a plane of the deformable layer, wherein the nano-scale protrusions are spaced apart from each other;
      a plurality of SERS-active nanoparticles disposed on the plurality of nano-scale protrusions, wherein the plurality of SERS-active nanoparticles are to be illuminated with light of a pump wavelength to cause Raman excitation light to interact with the nanoparticles and produce enhanced Raman scattered light from molecules located in close proximity to the nanoparticles, and wherein morphologies of the deformable layer and the plurality of nano-scale protrusions are to be controllably varied to modify an intensity of the Raman scattered light produced from the molecules;
   a first reflector disposed adjacent to the apparatus to partially reflect Raman scattered light emitted from an analyte introduced to the apparatus;
   a second reflector disposed adjacent to the apparatus opposite the first reflector to reflect the Raman scattered light; and
   a photodetector positioned to detect the Raman scattered light transmitted through the first reflector, wherein the Raman scattered light corresponds to a Raman spectrum associated with the analyte.

14. The analyte sensor according to claim 13, further comprising:
   an actuator to controllably vary the morphology of the deformable layer.

15. The analyte sensor according to claim 13, further comprising:
   a first actuator mechanically coupled to the first reflector and a second actuator mechanically coupled to the second reflector, wherein the first actuator is to control the reflectivity of the first reflector and the second actuator is to control the reflectivity of the second reflector.

16. The analyte sensor according to claim 13, wherein the apparatus further comprises a substrate having a plurality of nano-scale projections extending from a plane of the substrate and in a direction toward the deformable layer, wherein the plurality of nano-scale projections are spaced apart from each other; and
   wherein the plurality of nano-scale protrusions are formed in the deformable layer through contact by the plurality of nano-scale projections onto the deformable layer.

17. A method for performing Surface Enhanced Raman Spectroscopy (SERS) on a tunable apparatus having a deformable layer comprising a plurality of nano-scale protrusions extending from a plane of the deformable layer, wherein the plurality of nano-scale protrusions are spaced apart from each other and a plurality of SERS-active nanoparticles disposed on the plurality of nano-scale protrusions, said method comprising:
   arranging the deformable layer such that the plurality of nano-scale protrusions on the deformable layer have first morphologies;
   illuminating the plurality of nano-scale protrusions with light of a pump wavelength to cause Raman excitation light to interact with the nanoparticles and produce a first enhanced Raman scattered light from molecules located in close proximity to the nanoparticles;
   varying the morphologies of the plurality of nano-scale protrusions on the deformable layers such that the plurality of nano-scale protrusions on the deformable layer have second morphologies; and
   illuminating the plurality of nano-scale protrusions with light of a pump wavelength to cause Raman excitation light to interact with the nanoparticles and produce a second enhanced Raman scattered light from molecules located in close proximity to the nanoparticles.

18. The method according to claim 17, further comprising:
   detecting the first enhanced Raman scattered light and the second enhanced Raman scattered light.

19. The method according to claim 17, wherein varying the morphologies of the plurality of nano-scale protrusions on the deformable layer further comprises varying the morphologies of the plurality of nano-scale protrusions through application of at least one of a mechanical, electrical, thermal, and chemical interaction on the apparatus.

20. The method according to claim 17, further comprising:
   varying the morphologies of the plurality of nano-scale protrusions to cause the plurality of nano-scale protrusions to have additional morphologies;
   illuminating the plurality of nano-scale protrusions with light to produce additional enhanced Raman scattered light;
   detecting the enhanced Raman scattered light produced at multiple morphologies of the plurality of nano-scale protrusions; and
   determining which of the multiple morphologies of the one or more locations results in the highest Raman intensity.

* * * * *

UNITED STATES PATENT AND TRADEMARK OFFICE
CERTIFICATE OF CORRECTION

PATENT NO.        : 8,269,963 B2                           Page 1 of 1
APPLICATION NO.   : 12/771779
DATED             : September 18, 2012
INVENTOR(S)       : Fung Suong Ou et al.

It is certified that error appears in the above-identified patent and that said Letters Patent is hereby corrected as shown below:

In column 1, lines 16-17, delete "PCT/US2009/1052308," and
insert -- PCT/US2009/052308, --, therefor.

In column 11, line 9, delete "PCT/US20081083827" and insert -- PCT/US2008/083827 --, therefor.

Signed and Sealed this
Ninth Day of April, 2013

Teresa Stanek Rea
*Acting Director of the United States Patent and Trademark Office*